United States Patent [19]
Fauchere et al.

[11] Patent Number: 5,561,113
[45] Date of Patent: Oct. 1, 1996

[54] NEW PSEUDOPEPTIDE COMPOUNDS OF NEUROKININS

[75] Inventors: Jean-Luc Fauchere, Saint-Cloud; Nathalie Kucharczyk-Gentric, Issy Les Moulineaux; Joseph Paladino, Conflans Sainte Honorine; Jacqueline Bonnet; Emmanuel Canet, both of Paris; Graham Birrell, Garches, all of France

[73] Assignee: Adir ET Compagnie, Courbevoie, France

[21] Appl. No.: 427,802

[22] Filed: Apr. 26, 1995

[30] Foreign Application Priority Data

Apr. 28, 1994 [FR] France ................... 94.05137

[51] Int. Cl.$^6$ ............... A61K 38/05; C07D 257/04
[52] U.S. Cl. ............................... 514/19; 548/253
[58] Field of Search ................... 514/19; 548/253

[56] References Cited

FOREIGN PATENT DOCUMENTS

| | | |
|---|---|---|
| 0333174 | 9/1989 | European Pat. Off. . |
| 0394989 | 10/1990 | European Pat. Off. . |
| 9222569 | 12/1992 | WIPO . |

*Primary Examiner*—Jerry D. Johnson
*Attorney, Agent, or Firm*—The Firm of Gordon W. Hueschen

[57] ABSTRACT

A compound of formula (I):

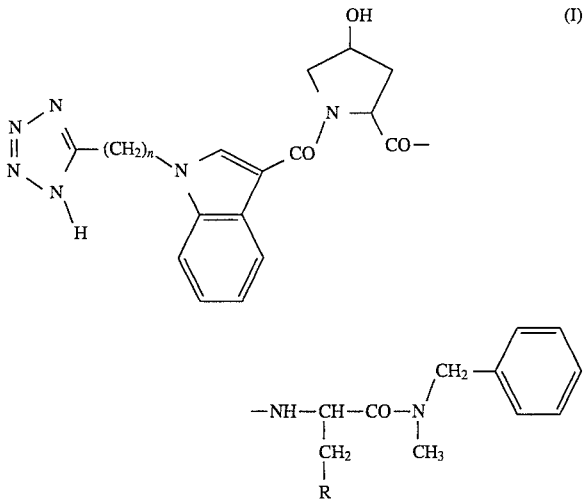

in which:

R represents naphthyl, 5,6,7,8-tetrahydronaphthyl, 1,2,3,4-tetrahydronaphthyl, thienyl, optionally substituted phenyl or ($C_3$–$C_7$)cycloalkyl, n represents an integer such that $1 \leq n \leq 8$, their enantiomers, diastereoisomers and epimers as well as their addition salts with a pharmaceutically acceptable acid or base and medicinal products containing the same are useful as antagonists of substance P.

7 Claims, No Drawings

NEW PSEUDOPEPTIDE COMPOUNDS OF NEUROKININS

TITLE OF THE INVENTION

New pseudopeptides compounds of neurokinines.

1. Field of the Invention

The present invention relates to new pseudopeptide compounds of neurokinins.

2. Description of the Prior Art

Neurokinins form a family of neuropeptides having, at the C-terminal part, a structural analogy: Phe-X-Gly-Leu-Met. These neuropeptides, substance (SP), neurokinin (NKA) and neurokinin (NKB), induce a rapid contraction of the smooth muscle fibers as opposed to the slow contractions developed by bradykinin. Widely represented in the human body, in particular in the central nervous system and the peripheral nervous system, their endogenous agonist effects occur via specific receptors with a preferential affinity for $NK_1$, $NK_2$, $NK_3$ respectively, for SP, NKA and NKB. They are involved in numerous physiological or physiopathological processes such as nociception, vasopermeability, contractions of the smooth muscle fibers, hypersecretions and immunomodulations (OTSUKA M. et al., Physiol. Rev. 73, 229–308, 1993).

Numerous peptides which are antagonists of neurokinins have been described in the literature. This is the case for example for the compounds described in Patents EP 333174, EP 394989 or WO 9222569.

SUMMARY OF THE INVENTION

The subject of the present invention is synthetic pseudopeptides which, in addition to the fact that they are new, have proved to be particularly valuable because of the intensity of their pharmacological properties. They possess selective and potent antagonistic properties towards the neurokinin receptors and more particularly the $NK_1$ receptors.

These properties render their use possible especially in the treatment of pain, inflammatory processes of various origins, gastrointestinal disorders, asthma, allergies, urological disorders, migraine and diseases of the central nervous system.

DETAILED DESCRIPTION OF THE INVENTION

The invention relates more particularly to new compounds of formula (I):

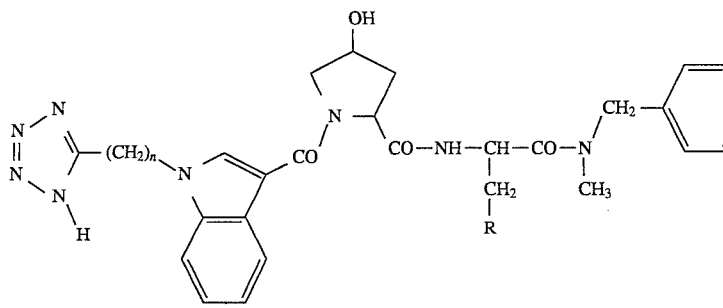

in which:
R represents a naphthyl, 5,6,7,8-tetrahydronaphthyl, 1,2,3,4-tetrahydronaphthyl, thienyl, phenyl (optionally substituted by one or more halogen atoms or linear or branched ($C_1$–$C_6$) alkyl, linear or branched ($C_1$–$C_6$) alkoxy, hydroxyl or trihalomethyl groups) or ($C_3$–$C_7$) cycloalkyl group, n represents an integer such that $1 \leq n \leq 8$, their enantiomers, diastereoisomers and epimers as well as their addition salts with a pharmaceutically acceptable acid or base.

Among the pharmaceutically acceptable acids, there may be mentioned, with no limitation being implied, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric acids and the like.

Among the pharmaceutically acceptable bases, there may be mentioned, with no limitation being implied, sodium hydroxide, potassium hydroxide, triethylamine, tertbutylamine and the like.

The invention also extends to the process for preparing the compounds of formula (I), wherein a protected hydroxyproline, of formula (II), whose isomers have optionally been separated:

in which:

Fmoc represents the 9-fluorenylmethoxycarbonyl group,
tBu represents the tert-butyl group, is reacted with benzyl alcohol, in the presence of 4-dimethylaminopyridine and N,N-dicyclohexylcarbodiimide, to give the compound of formula (III):

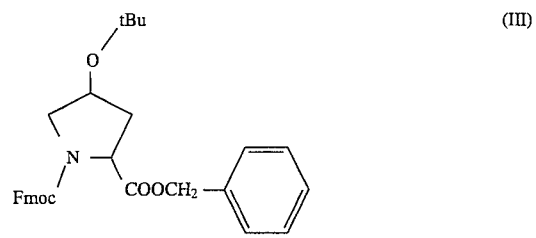

in which Fmoc and tBu have the same meanings as above, whose amine functional group is deprotected in piperidine medium, to give the compound of formula (IV):

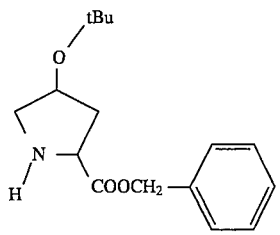

in which tBu has the same meaning as above, which is reacted with indole-3-carboxylic acid, to give the compound of formula (V):

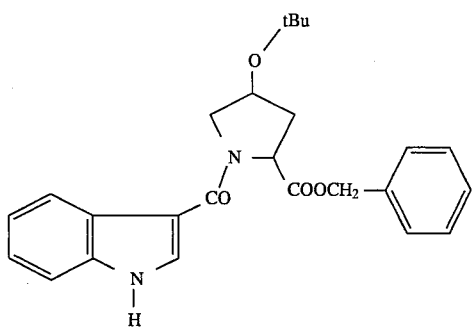

in which tBu has the same meaning as above, whose carboxylic acid functional group is deprotected, by catalytic hydrogenation, to give the compound of formula (VI):

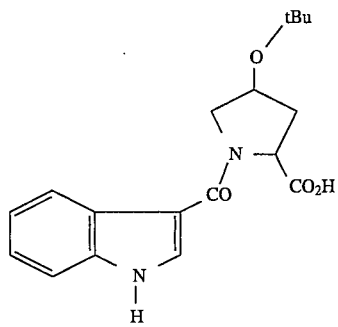

in which tBu has the same meaning as above, which is reacted with a protected amino acid of formula (VII), whose isomers are optionally separated:

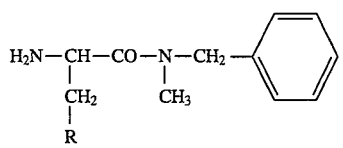

in which R has the same meaning as in formula (I), to give the compound of formula (VIII):

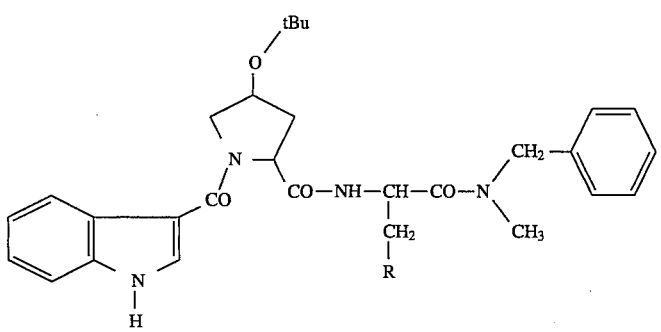

in which tBu and R have the same meaning as above, which is reacted with a protected tetrazole of formula (IX), in the presence of tetrabutylammonium hydrogen sulfate,

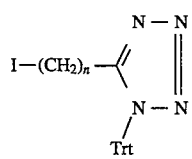

in which Trt represents the triphenylmethyl group, to give the compound of formula (X):

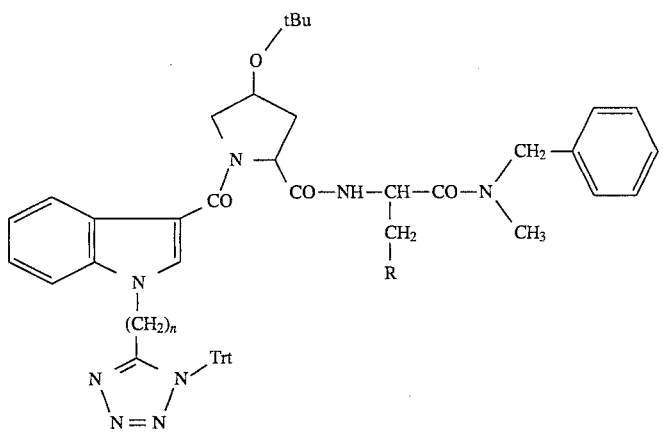

(X)

in which tBu, R and Trt have the same meaning as above, which is deprotected, in trifluoroacetic acid medium, to give the compound of formula (I), which may be, where appropriate, purified according to a conventional purification technique, whose isomers are, where appropriate, separated according to a conventional separation technique, which is converted, if desired, into its addition salts with a pharmaceutically acceptable base.

The compound of formula (VII) is obtained by the reaction of a protected amino acid of formula (XI):

(XI)

in which R has the same meaning as in formula (I) and Boc represents a tert-butoxycarbonyl group, with N-methylbenzylamine, according to a conventional peptide coupling reaction such as that described by W. KONIG and R. GEIGER (Ber., 103, 788, 1970), to give the compound of formula (XII):

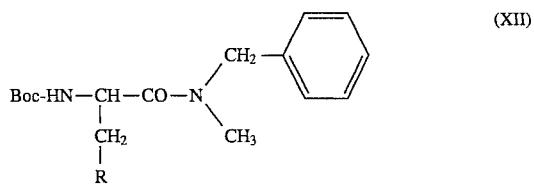

(XII)

in which Boc and R have the same meaning as above, which is deprotected in hydrochloric medium, to give the compound of formula (VII).

The compound of formula (IX) is obtained by the reaction of a nitrile of formula (XIII):

(XIII)

in which n has the same meaning as in formula (I), with sodium azide, in the presence of aluminum chloride, under an inert atmosphere, to give the compound of formula (XIV):

(XIV)

in which n has the same meaning as in formula (I), which is reacted with triphenylmethyl chloride in the presence of triethylamine, to give the compound of formula (XV):

(XV)

in which n and Trt have the same meaning as above, which is then treated with sodium iodide, to give the corresponding iodinated compound of formula (IX).

The compounds of the invention possess very valuable pharmacological properties. They are specific ligands of the neurokinin receptors which possess in particular particularly intense antagonistic properties towards the $NK_1$ receptors. The $NK_1$ receptors are thought to be more particularly involved in the regulation of pain transmission, edema induced by an increase in vasopermeability, secretory phenomena at the tracheobronchial and gastrointestinal level, salivation, ventilatory control and control of vascular tonus, and the activation of the cells participating in inflammatory processes. Furthermore, unlike certain pseudopeptide compounds which are antagonists of substance P, these compounds lack degranulating effect on the mast cells.

The subject of the present invention is also the pharmaceutical compositions containing, as active ingredient, at least one compound of formula (I), alone or in combination with one or more nontoxic inert excipients or vehicles.

Among the pharmaceutical compositions according to the invention, there may be mentioned more particularly those which are suitable for oral, parenteral or nasal administration, simple or sugar-coated tablets, sublingual tablets, gelatin capsules, lozenges, suppositories, creams, ointments, skin gels and the like.

The useful dosage varies according to the age and the weight of the patient, the nature and the severity of the condition as well as the route of administration. This may be oral, nasal, rectal or parenteral. In general, the unit dosage varies between 0.2 and 100 mg for a treatment of 1 to 3 doses per 24 hours.

The following examples illustrate the invention and do not limit it in any manner. The starting materials used are known materials or materials prepared according to known procedures.

Preparations A and B do not give the compounds of the invention but synthesis intermediates which are useful in the preparation of the compounds of formula (I).

In the examples and preparations below, the amino acids of which the abbreviations start with an upper case letter are of L configuration. The amino acids of which the abbreviations start with a lower case letter are of D configuration.

The abbreviations used in the examples and the preparations are the following:

Nal-NMeBzl represents the residue (L)-N-methylbenzylamino-naphth-2-ylalanyl of formula:

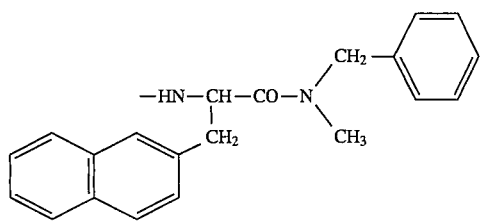

Tna-NMeBzl represents the residue (L)-N-methylbenzylamino-5,6,7,8-tetrahydronaphth- 2-ylalanyl of formula:

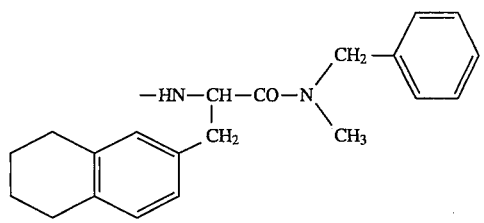

Thn-NMeBzl represents the residue (L)-N-methylbenzylamino-1,2,3,4-tetrahydronaphth- 2-ylalanyl of formula:

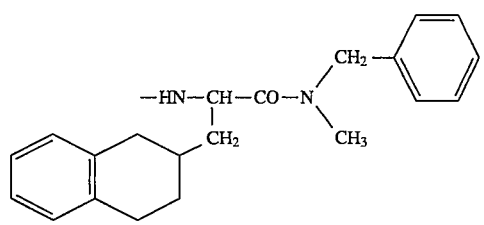

Thi-NMeBzl represents the residue (L)-N-methylbenzylamino-thien-2-ylalanyl of formula:

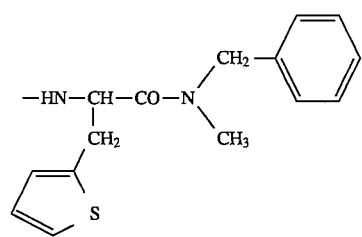

Phe represents the phenylalanyl residue,
Cha-NMeBzl represents the residue (L)-N-methylbenzylamino-cyclohexylalanyl of formula:

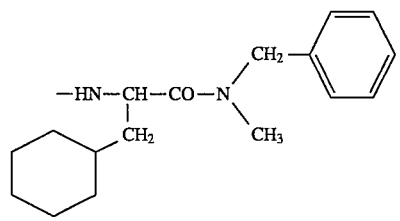

Boc represents the tert-butoxycarbonyl group,
Hyp represents the residue (R)-4-hydroxy-L-prolyl of formula:

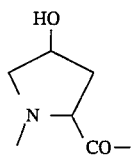

Fmoc represents the 9-fluorenylmethoxycarbonyl group
tBu represents the tert-butyl group
H-Hyp(tBu)-OBzl represents the residue of formula:

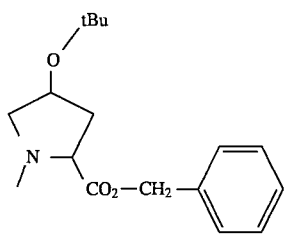

Preparation A: H-Nal-NMeBzl, hydrochloride

Stage A: (L)-Boc-Nal-NMeBzl 12.6 mmol of (L)-Boc-Nal-OH, 13.9 mmol of 2-(1H-benzotriazol-1-yl)-1,1,3,3 -tetramethyluronium tetrafluoroborate and then 12.6 mmol of N-methylbenzylamine are successively added to 30 cm$^3$ of dichloromethane. 27.7 mmol of N,N-diisopropylethylamine are added to the mixture maintained stirring on an ice bath. After stirring for 1 hour at 0° C., the mixture is adjusted to room temperature and maintained stirring for 20 hours. After concentration, the residual oil is taken up in ethyl acetate. The solution is washed with sodium bicarbonate, then with a 5% citric acid solution and finally with a saturated sodium chloride solution. The dried and evaporated organic phase gives the expected product in the form of an oil.

Stage B: H-Nal-NMeBzl, hydrochloride

The expected product is obtained by treating the product obtained in the preceding stage with a 6N hydrochloric acid solution in ethyl acetate, for 90 minutes. After evaporation of the solvent, the solid obtained is taken up in ether and then in pentane. The expected product is then obtained by filtration of the precipitate and drying of the latter.

Preparation B: 5-(4-iodobutyl)-1-triphenylmethyl-1H-tetrazole

Stage A: 5-(4-chlorobutyl)tetrazole

100mmol of 5-chlorovaleronitrile are placed under an inert atmosphere in 100 ml of anhydrous tetrahydrofuran on an ice bath. 445 mmol of sodium azide and then 100 mmol of aluminum chloride are then added in small fractions. The reaction mixture is heated to 80° C. and left under reflux, with stirring, for 16 hours. The complex formed is then hydrolyzed by addition, dropwise, of 150 cm$^3$ of 5% hydrochloric acid. The resulting aqueous phase is extracted with ethyl acetate and after washing the organic phase with water, then with a saturated sodium chloride solution, drying and evaporation, the residue obtained is taken up in pentane. The expected product is then obtained after filtration of the precipitate formed.

Stage B:
5-(4-chlorobutyl)-1-triphenylmethyl-1H-tetrazole 68 mmol of triethylamine and then 68 mmol of triphenylmethyl chloride are successively added to a solution containing 68 mmol of the compound obtained in the preceding stage in 80 ml of chloroform. The solution is left for 15 hours, with stirring, at room temperature. After evaporation, the residual oil is taken up in ethyl acetate. The solution is washed with 5% sodium bicarbonate, then with 5% citric acid and finally with a saturated sodium chloride solution. After drying and evaporation, the expected product, in the form of a solid, is obtained after taking up in penlane, filtration and drying.

Stage C:
5-(4-iodobutyl)-1-triphenylmethyl-1H-tetrazole 25 mmol of sodium iodide are added to 25 mmol of the compound obtained in the preceding stage in 100 ml of anhydrous acetone. The mixture is heated to 60° C. and left for 15 hours under reflux. After filtration of the precipitate formed, the filtrate concentrated under vacuum gives the expected product.

EXAMPLE 1:
{1-[4-(1H-tetrazol-5-yl)butyl]indol-3-yl}carbonyl-Hyp-Nal-NMeBzl, potassium salt

Stage A: Fmoc-Hyp(tBu)-OBzl 65 mmol of N,N-dicyclohexylcarbodiimide are added to a mixture containing 61 mmol of Fmoc-Hyp(tBu)-OH, 65 mmol of benzyl alcohol and 27 mmol of 4-dimethylaminopyridine in 150 ml of dichloromethane cooled on an ice bath. After one hour at 0° C., the mixture is adjusted to room temperature and left stirring for 18 hours. The dicyclohexylurea precipitate is filtered and the filtrate is evaporated. The residual oil is taken up in ethyl acetate. The solution is washed with 5% sodium bicarbonate, with 5% citric acid and then with a saturated sodium chloride solution. After drying and evaporation, the expected product is obtained in the form of an oil.

Stage B: H-Hyp(tBu)-OBzl

The oil obtained in the preceding stage is treated with 240 ml of a 20% solution of piperidine in ethyl ether, for 2 hours 30 minutes. After concentration, the residual oil is purified by silica column chromatography using ethyl acetate as eluent and gives the expected product in the form of an oil.

Stage C: (Indol-3-yl)carbonyl-Hyp(tBu)-OBzl 100 mmol of N,N-diisopropylethylamine are added to a mixture containing 50 mmol of the product obtained in the preceding stage, 65 mmol of indole-3-carboxylic acid and 75 mmol of bromo-tris-pyrrolidino-phosphonium hexafluorophosphate in 80 mmol of dichloromethane cooled on an ice bath. After 30 minutes at 0° C., the mixture is adjusted to room temperature and maintained stirring for 17 hours. After evaporation, the residual oil is taken up in ethyl acetate. The solution is washed with 5% sodium bicarbonate, with 5% citric acid and with a saturated sodium chloride solution. The expected product crystallizes and is isolated by filtration.

Stage D: (Indol-3-yl)carbonyl-Hyp(tBu)-OH 23 mmol of the product obtained in the preceding stage are dissolved, with the use of heat, in 1 liter of anhydrous methanol. After returning to room temperature, under an inert atmosphere, 50 ml of glacial acetic acid and 1 g of 1% palladium on charcoal are added. The suspension is hydrogenated for 20 hours at room temperature and at atmospheric pressure.

The catalyst is then filtered, rinsed with methanol and the filtrate is evaporated. The residue is taken up in ethyl acetate and gives the expected product which crystallizes and is filtered.

Stage E:
(Indol-3-yl)carbonyl-Hyp(tBu)-Nal-NMeBzl 21 mmol of N,N-diisopropylethylamine are added to a mixture containing 9.5 mmol of the product obtained in the preceding stage, 10.5 mmol of the compound described in preparation A, 10.5mmol of 2-(1H-benzotriazol-1-yl)-1,1,3,3-tetramethyluronium tetrafluoroborate, 10.5 mmol of hydroxybenzotriazole in 50 ml of dichloromethane cooled on an ice bath. After one hour at 0° C., the mixture is adjusted to room temperature and stirred for 16 hours. After concentration, the residue is taken up in ethyl acetate. The solvent is washed with 5% sodium bicarbonate, 5% citric acid and with a saturated sodium chloride solution. The expected product crystallizes and is filtered.

Stage F: {1-[4-(4-triphenylmethyl-1H-tetrazol-5-yl)butyl]indol-3-yl}carbonyl-Hyp(tBu)-Nal-NMeBzl 19 mmol of sodium hydroxide in the form of finely ground pellets are added to a solution containing 4.76 mmol of the compound obtained in the preceding stage and 0.05 mmol of tetrabutylammonium hydrogen sulfate in 70 ml of dichloromethane. The suspension is stirred for 5 minutes and 14.3 mmol of the compound obtained in preparation B are added. The whole is maintained stirring for 24 hours. After evaporation of the solvent, the residue is taken up in ethyl acetate. The solution is washed with 5% sodium bicarbonate, 5% citric acid and then with a saturated sodium chloride solution. After drying and evaporation, the residue is purified by silica column chromatography using ethyl acetate as eluent and gives the expected product in the form of a powder.

Stage G:
{1-[4-(1H-tetrazol-5-yl)butyl]indol-3-yl}carbonyl-Hyp-Nal-NMeBzl 3.01 mmol of the compound obtained in the preceding stage are treated with 500 ml of a trifluoroacetic acid/dichloromethane mixture (50/50), at room temperature, for 3 hours. After concentration, the residual oil is taken up in an ethyl ether/pentane mixture and gives a precipitate which is filtered and purified by preparative HPLC on a $C_{18}$ reversed phase using as solvent a water/acetonitrile system in which the percentage of acetonitrile varies from 30% to 40% over 1 hour. This purification gives the expected product which is freeze-dried.

Stage H: {1-[4-(1H-tetrazol-5-yl)butyl]indol-3-yl}carbonyl-Hyp-Nal-NMeBzl, potassium salt The potassium salt of the product described in the preceding stage is obtained by addition of 2.08 mmol of a 0.1N potassium hydroxide solution to a cooled solution containing 1.89 mmol of the compound obtained in the preceding stage in a water/acetonitrile mixture. This salt is then freeze-dried.

Elemental microanalysis:

|  | C % | H % | N % |
|---|---|---|---|
| calculated | 60.20 | 5.89 | 13.96 |
| found | 59.82 | 5.58 | 13.61 |

Example 2:
{1-[4-(1H-tetrazol-5-yl)butyl]indol-3-yl}carbonyl-Hyp-Tna-NMeBzl, potassium salt and

Example 3:
{1-[4-(1H-tetrazol-5-yl)butyl]indol-3-yl}carbonyl-Hyp-Thn-NMeBzl, potassium salt

Stage A: (L)-Boc-Tna-NMeBzl and [(L,L)+(L,D)]-Boc-Thn-NMeBzl 10 drops of glacial acetic acid and then 1.5 g of palladium on charcoal are successively added to a solution of 7.17 mmol of (L)-Boc-Nal-NMeBzl in 20 cm³ of methanol. The mixture is hydrogenated for 3 days at room temperature and at atmospheric pressure. After removal of the catalyst by filtration and evaporation of the solvent, the expected products are obtained in the form of a colorless oil, in the proportions: (L)-Boc-Tna-NMeBzl/(L,L)-Boc-Thn-NMeBzl/(L,D)-Boc-Thn-NMeBzl: 60/20/20.

Stage B: H-Tna-NMeBzl, trifluoroacetate+H-Thn-NMeBzl, trifluoroacetate

The preceding oil is treated with 100 cm³ of a trifluoroacetic acid/dichloromethane mixture (50/50) and left stirring at room temperature for 2 hours. After concentration under vacuum and trituration in pentane, the deprotected mixture is obtained in the form of an oil.

Stage C: (Indol-3-yl)carbonyl-Hyp(tBu)-Tna-NMeBzl+(Indol-3-yl)carbonyl-Hyp(tBu)-Thn-NMeBzl 4.4 mmol of N,N-diisopropylethylamine are added to a mixture containing 2 mmol of (indol-3-yl)carbonyl-Hyp(tBu)-OH, 2 mmol of the compound described in the preceding stage B, 2.2 mmol of BTUT, 2.2 mmol of HOBt in 10 ml of dichloromethane. The resulting solution is left stirring for 8 hours and is then taken up in ethyl acetate. After washing the organic phase with water, 5% sodium bicarbonate, 5% citric acid and with a saturated sodium chloride solution, drying and concentration under vacuum, the crystalline foam obtained is purified on silica with the 100% ethyl acetate eluent.

An additional purification by preparative HPLC on a $C_{18}$ reversed phase, using eluents A: water/trifluoroacetic acid 0.1%; B: acetonitrile/trifluoroacetic acid 0.1% in a 35% of B to 65% of B gradient over 90 minutes, makes it possible to separate the two derivatives containing either Tna, or Thn. Under these conditions on the other hand, it was not possible to separate the two diastereoisomers of the Thn adduct.

Example 2:
{1-[4-(1H-tetrazol-5-yl)butyl]indol-3-yl]carbonyl-Hyp-Tna-NMeBzl, potassium salt The expected product is prepared according to procedures F, G and H of Example 1 from (indol-3-yl)carbonyl-Hyp(tBu)-Tna-NMeBzl obtained in the preceding stage C.

Elemental microanalysis:

|  | C % | H % | N % |
|---|---|---|---|
| calculated | 64.84 | 6.12 | 15.12 |
| found | 65.32 | 5.88 | 14.46 |

FAB mass spectrum: $[M+H]^+$ m/z=741

Example 3:
{1-[4-(1H-tetrazol-5-yl)butyl]indol-3-yl}carbonyl-Hyp-Thn-NMeBzl, potassium salt The expected product is prepared according to procedures F, G and H of Example 1 from (indol-3-yl)carbonyl-Hyp(tBu)-Thn-NMeBzl obtained in the preceding stage C.
FAB mass spectrum: $[M+H]^+$ m/z=741

Example 4:
{1-[(1H-tetrazol-5-yl)methyl]indol-3-yl}carbonyl-Hyp-Nal-NMeBzl, potassium salt This compound was prepared according to the same procedure as that in Example 1, using 5-iodomethyl-1-triphenylmethyl-1H-tetrazole obtained according to preparation B from chloroacetonitrile. Elemental microanalysis:

|  | C % | H % | N % |
|---|---|---|---|
| calculated | 63.96 | 5.08 | 16.13 |
| found | 63.57 | 5.01 | 15.93 |

FAB mass spectrum: $[M+H]^+$ m/z=695

Example 5:
{1-[2-(1H-tetrazol-5-yl)ethyl]indol-3-yl}carbonyl-Hyp-Nal-NMeBzl, potassium salt

Stage A: [1-(2-cyanoethyl)indol-3-yl]carbonyl-Hyp(tBu)-Nal-NMeBzl 1.58 mmol of sodium hydride are added in small portions to a solution containing 0.79 mmol of (indol-3-yl)carbonyl-Hyp(tBu)-Nal-NMeBzl (stage E of Example 1) and 0.87 mmol of 3-bromopropionitrile in 10 ml of anhydrous tetrahydrofuran. After stirring for 24 hours at room temperature, the solvent is removed under vacuum and the residue taken up in ethyl acetate. The resulting solution is washed with water, 5% sodium bicarbonate, 5% citric acid and with a saturated sodium chloride solution and then dried over $Na_2SO_4$. After evaporation of the solvent, the mixture is purified by flash chromatography on silica with the eluent dichloromethane/acetone 80/20. The fractions are concentrated under vacuum to give the expected product in the form of a white powder.

Stage B:
[1-[2-(1H-tetrazol-5-yl)ethyl]indol-3-yl]carbonyl-Hyp(tBu)-Nal-NMeBzl 1.75 mmol of trimethylsilyl azide and 0.09 mmol of dibutyltin oxide are added to a solution containing 0.44 mmol of the peptide obtained in the preceding stage in 10 ml of toluene. The reaction mixture is maintained stirring at 80° C. for 24 hours and then the toluene is evaporated. The residue is taken up twice in methanol and then concentrated under vacuum and taken up in ethyl acetate. The solution is washed with 5% citric acid and with a saturated sodium chloride solution, dried over $Na_2SO_4$ and concentrated under vacuum to give the expected product in the form of a white powder.

Stage C:
{1-[2-(1H-tetrazol-5-yl)ethyl]indol-3-yl}carbonyl-Hyp-Nal-NMeBzl 0.35 mmol of the compound obtained in the preceding stage are treated with 20 ml of a trifluoroacetic acid/dichloromethane mixture (50/50) at room temperature for 5 hours. After concentration, the resulting oil is taken up in ethyl ether and gives a precipitate which is filtered and purified by preparative HPLC on a $C_{18}$ reversed phase using as solvent a water/acetonitrile system in which the percentage of acetonitrile varies from 35% to 50% over 30 min. This purification gives the product which is freeze-dried.

Stage D:
{1-[2-(1H-tetrazol-5-yl)ethyl]indol-3-yl}carbonyl-Hyp-Nal-NMeBzl, potassium salt The potassium salt of the product described in the preceding stage is obtained by addition of 0.111 mmol of a 0.1N potassium hydroxide solution to a cooled solution of 0.110 mmol of the compound obtained in the preceding stage in a water/acetonitrile mixture. This salt is then freeze-dried.

| | Elemental microanalysis: | | |
|---|---|---|---|
| | C % | H % | N % |
| calculated | 64.39 | 5.26 | 15.81 |
| found | 63.75 | 5.00 | 15.26 |

FAB mass spectrum: $[M+H]^+$ m/z=709

Example 6:
[1-[3-(1H-tetrazol-5-yl)propyl]indol-3-yl}carbonyl-Hyp-Nal-NMeBzl, potassium salt This compound was prepared according to the same procedure as that in Example 1, using 5-(3-iodopropyl)-1-triphenylmethyl-1H-tetrazole obtained as described in preparation B from 4-chlorobutyronitrile.

| | Elemental microanalysis: | | |
|---|---|---|---|
| | C % | H % | N % |
| calculated | 64.80 | 5.44 | 15.50 |
| found | 64.78 | 5.24 | 15.27 |

FAB mass spectrum: $[M+H]^+$ m/z=723

Example 7:
{1-[5-(1H-tetrazol-5-yl)pentyl]indol-3-yl}carbonyl-Hyp-Nal-NMeBzl, potassium salt This product was prepared according to the same procedure as that for the compound of Example 5, starting with 6-bromocapronitrile.

| | Elemental microanalysis: | | |
|---|---|---|---|
| | C % | H % | N % |
| calculated | 65.58 | 5.77 | 14.92 |
| found | 64.85 | 5.61 | 14.38 |

FAB mass spectrum: $[M+H]^+$ m/z=751

Examples 8 to 11 were prepared according to the procedure described in Example 1 from the corresponding starting materials obtained according to the procedure described in preparation A.

Example 8:
{1-[4-(1H-tetrazol-5-yl)butyl]indol-3-yl}carbonyl-Hyp-Thi-NMeBzl, potassium salt

| | Elemental microanalysis: | | |
|---|---|---|---|
| | C % | H % | N % |
| calculated | 59.02 | 5.24 | 16.20 |
| found | 59.02 | 5.12 | 15.68 |

FAB mass spectrum: $[M+H]^+$ m/z=655

Example 9:
{1-[4-(1H-tetrazol-5-yl)butyl]indol-3-yl}carbonyl-Hyp-(4-chloro)Phe-NMeBz potassium salt FAB mass spectrum: $[M+H]^+$ m/z=721

Example 10:
{1-[4-(1H-tetrazol-5-yl)butyl]indol-3-yl}carbonyl-Hyp-(3,4-dimethoxy)Phe-NMeBzl, potassium salt FAB mass spectrum: $[M+H]^+$ m/z=747

Example 11:
{1-[4-(1H-tetrazol-5-yl)butyl]indol-3-yl}carbonyl-Hyp-Cha-NMeBzl, potassium salt FAB mass spectrum: $[M+H]^+$ m/z=693

Pharmacological study of the compounds of the invention

Example 12: Affinity for the human receptors $NK_1$ and $NK_2$

The affinity for the human receptors $NK_1$ and $NK_2$ was studied on the human lymphoblasts IM-9 specifically expressing the $NK_1$ receptor as described by D. G. PAYAN et al. (J. Biol. Chem. 1986, 261, 14321–14329) and on CHO-K1 cells transfected with the $NK_2$ receptor based on the "CellPhect transfection" kit (Pharmacia).

The compounds of the invention showed an excellent affinity specific for the $NK_1$ receptors. The results are presented in the table below:

| Example | NK$_1$ (IM-9) KI nM | NK$_2$ (CHO) KI nM |
|---------|---------------------|---------------------|
| 1 | 0.04 | 2400 |
| 2 | 14 | 3600 |
| 3 | 14 | 1400 |
| 4 | 0.78 | >1000 |
| 5 | 0.63 | >10000 |
| 6 | 1.2 | >1000 |
| 7 | 5.9 | 10000 |
| 8 | 110 | >1000 |
| 9 | 22 | 3900 |
| 10 | 180 | >10000 |
| 11 | 52 | >1000 |

Example 13: Trial on isolated smooth muscle

In order to evaluate the functional activity of the compounds of the invention as antagonists of neurokinins, three preparations isolated from smooth muscle were used: rabbit vena cava (RVC), endothelium-free rabbit pulmonary artery (RPA) and rat portal vein (RatPV) whose contractile responses are respectively mediated by the NK$_1$, NK$_2$ and NK$_3$ receptors as indicated by D. JUKIC et al. (Life Sci. 1991, 49, 1463–1469).

The antagonistic power of the compounds of the invention was expressed in the form of pA$_2$ as defined by O. ARUNLAKSHANA and H. O. SCHILD (Brit. J. Pharmacol. 1959, 14, 48–58).

The compounds of the invention showed a potent antagonistic activity towards the NK$_1$ receptors with a low activity for the NK$_2$ and NK$_3$ receptors. The results obtained for Examples 1, 2 and 3 are presented in the table below:

| Example | NK$_1$ (VCL) pA$_2$ | NK$_2$ (APL) pA$_2$ | NK$_3$ (VPR) pA$_2$ |
|---------|---------------------|---------------------|---------------------|
| 1 | 9.57 | 5.57 | 4.96 |
| 2 | 8.17 | 6.47 | 5.87 |
| 3 | 7.87 | 5.87 | 5.87 |
| 4 | 8.14 | — | 5.84 |
| 6 | 8.46 | 5.20 | — |
| 7 | 7.88 | — | — |

Example 14: Study of the antinociceptive potential—Eddy's test in mice

Because of the involvement of substance P in nociceptive transmission at the spinal level (M. OTSUKA and S. KONISHI, TINS, 6, 317–320, 1983) and more particularly in pain of thermal origin (A. W. DUGGAN et al., Brain Research, 1987, 403, 345–349), the in vivo pharmacological activity of the compounds of the invention was investigated in mice by the thermal hyperalgesia test initially described by N. B. EDDY et al. (J. Pharmacol. Exp. Ther., 1953, 107, 385–393). This test consists in measuring the reaction time to heat which is determined by the licking of the hind legs in mice (CD1 male, Ch. River, 25–30 g) placed on a metal plate heated to 55° C.

The animals were treated with the compounds of the invention intravenously, 10 minutes before passing over the hot plate.

The mean reaction time obtained for each treated batch (12 mice per batch) was compared with the mean for the corresponding control batch. The results are expressed in the form of ED$_{50}$ which corresponds to the dose which increases the reaction time by 50%.

Whereas intraspinally administered substance P decreases the reaction time of the animal, the compounds of the invention increased this reaction time after intravenous injection. For example, the compound of Example 1 had an ED$_{50}$ of 0.018 mg/kg (confidence interval for P=0.05: 0.001–0.322), the ED$_{50}$ of morphine being 0.30 mg/kg (0.03–2.90). Contrary to that of morphine, the activity of the compounds was not antagonized by naloxone.

Example 15: Study of the inhibition of plasma extravasation induced by substance P in guinea pigs The effect of the compounds on plasma extravasation caused by intravenous injection of substance P (1 µg/kg) in guinea pigs was evaluated on the bladder, according to the method described for rats by C. GARRET et al. (Proc. Natl. Acad. Sci., USA 1991, 88, 10208–20212). Vesical accumulation of Evans blue injected IV at the same time as substance P and 10 minutes before sacrificing, was quantified by spectrophotometry after extraction of the colorant with acetone. The inhibitory activity of the compounds administered intravenously 5 minutes before substance P was expressed as % inhibition compared with a control batch (8 animals per batch). By way of example, the compound of Example 1 exerted an activity of 56% at the dose of 0.1 mg/kg.

Example 16: Study of inhibition of the bronchoconstriction induced by substance P in guinea pigs The study is carried out on male Hartley guinea pigs (Charles River) of a mean weight of 300 to 400 g. The study is carried out on anesthetized animals (ethyl carbamate 1.5 g/kg) which are flaxedil curarized (0.2 mg/kg iv), ventilated with a frequency of 60 per minute and a standard volume of 10 ml/kg. The animals were pretreated with pyrilamine (1 mg/kg iv), propanolol (1 mg/kg iv).

The criterion for assessing the bronchoconstriction is the increase in the tracheal insufflation pressure (TIP) induced by the injection of substance P via the iv route at the dose of 2 nM/kg iv, each animal being its own control. The injection of the test product being carried out relative to the time TO injection of the product.

The results are expressed as percentage inhibition of the substance P-induced bronchoconstriction, this percentage being calculated according to the following formula:

($\Delta$TIP before product–$\Delta$TIP after product)/$\Delta$TIP before product (expressed as percentage).

The results are presented in the table below:

| Example | % Inhibition dose of 1 µmol/kg i.v. |
|---------|-------------------------------------|
| 1 | 95% |
| 4 | 61% |
| 6 | 60% |
| 7 | 58% |

Example 17: Study of mast cell degranulation in vitro

The studies are carried out on peritoneal mast cells of male rats: Sprague-Dawley of mean weight 350 to 400 g and are killed by euthanasia by inhalation of $CO_2$. A peritoneal lavage is carried out with 20 ml of buffer (NaCl 150 mM, KCl 2.7 mM, CaCl$_2$, 0.9 mM, Na$_2$HPO$_4$, 3 mM, KH$_2$PO$_4$, 3.5 mM, glucose 5.6 mM, bovine serum albumin 1 mg/ml, pH 6.8).

The lavage liquid is centrifuged at 400 g for 10 min at 4° C. and taken up in a buffer at a density of 2×10$^4$ mast cells/ml. The compounds are incubated at an increasing concentration for 20 min. The reaction is stopped by placing the tubes on ice and a centrifugation is carried out with 700 g for 10 min at 4° C. The supernatant and the pellet are tested by fluorimetry after condensation with o-phthaldehyde. The histamine released from the cells into the supernatant thus assayed is expressed as percentage of the total histamine content of the cells. During this test, the compound of Example 1 does not cause mast cell degranulation up to the concentration of 10$^{-4}$M.

Pharmaceutical composition

Example 18: Tablet: formula for the preparation of 1,000 tablets containing 2 mg doses

| | |
|---|---|
| Compound of Example 1 | 2 g |
| Hydroxypropyl cellulose | 2 g |
| Wheat starch | 10 g |
| Lactose | 100 g |
| Magnesium stearate | 3 g |
| Talc | 3 g |

We claim:

1. A compound of formula (I):

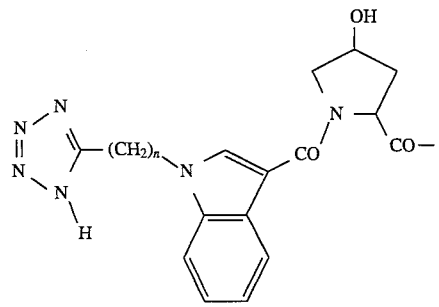

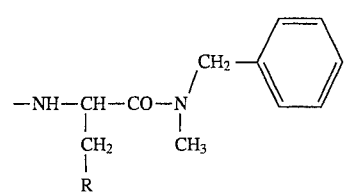

in which:

R represents (C$_3$–C$_7$)cycloalkyl, naphthyl, 5,6,7,8-tetrahydronaphthyl, 1,2,3,4-tetrahydronaphthyl, thienyl, or phenyl optionally substituted by one or more halogen or linear or branched (C$_1$–C$_6$)alkyl, linear or branched (C$_1$–C$_6$)alkoxy, hydroxyl, or trihalomethyl, n represents an integer such that $1 \leq n \leq 8$, their enantiomers, diastereoisomers and epimers, as well as their addition salts with a pharmaceutically-acceptable acid or base.

2. A compound of claim 1, wherein n is equal to 4.

3. A compound of claim 1, wherein R represents naphthyl.

4. A compound of claim 3, wherein R represents 2-naphthyl.

5. A compound of claim 1, which is selected from {1-[4-(1H-tetrazol-5-yl)butyl]indol-3-yl}carbonyl-Hyp-Nal-NMeBzl and its corresponding potassium salt.

6. A method for treating a mammal afflicted with a condition requiring an antagonist of substance P comprising the step of administering to the mammal an amount of a compound of claim 1 which is effective for alleviation of said condition.

7. A pharmaceutical composition useful as a substance pantagonist comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO.   : 5,561,113
DATED        : October 1, 1996
INVENTOR(S)  : J. Fauchere; N. Kucharczyk-Gentric;
               J. Paladino; J. Bonnet; E. Canet;
               G. Birrell It is certified that error appears in the above-indentified patent and that said Letters Patent is hereby corrected as shown below:

Title Page, [73] Assignee: "Adir ET Compagnie," should read --ADIR ET COMPAGNIE,--.

Column 9, line 13:  "penlane," should read -- pentane, --

Column 17, line 6:  "cells/mi" should read -- cells/ml --

Signed and Sealed this

Third Day of December, 1996

BRUCE LEHMAN

Attest:

Attesting Officer

Commissioner of Patents and Trademarks